United States Patent
Pindl

(10) Patent No.: US 10,442,682 B2
(45) Date of Patent: Oct. 15, 2019

(54) APPARATUS HAVING A CAVITY STRUCTURE AND METHOD FOR PRODUCING SAME

(71) Applicant: Infineon Technologies AG, Neubiberg (DE)

(72) Inventor: Stephan Pindl, Ergoldsbach (DE)

(73) Assignee: Infineon Technologies AG, Neubiberg (DE)

(*) Notice: Subject to any disclaimer, the term of this patent is extended or adjusted under 35 U.S.C. 154(b) by 0 days.

(21) Appl. No.: 15/927,574

(22) Filed: Mar. 21, 2018

(65) Prior Publication Data

US 2018/0273373 A1   Sep. 27, 2018

(30) Foreign Application Priority Data

Mar. 22, 2017 (DE) .................. 10 2017 204 817

(51) Int. Cl.
| | | |
|---|---|---|
| H01L 31/058 | (2006.01) | |
| B81B 7/00 | (2006.01) | |
| B81C 1/00 | (2006.01) | |
| H01L 23/34 | (2006.01) | |
| G01N 29/24 | (2006.01) | |

(52) U.S. Cl.
CPC ........ *B81B 7/0038* (2013.01); *B81C 1/00047* (2013.01); *B81C 1/00285* (2013.01); *G01N 29/2418* (2013.01); *H01L 23/345* (2013.01); *B81B 2207/096* (2013.01); *H01L 2224/16225* (2013.01)

(58) Field of Classification Search
CPC ... B81B 7/0041; B81B 7/0045; B81B 7/0048; B81B 2203/0315; B81C 1/00047; B81C 1/00277; B81C 1/00325; H01L 21/52; H01L 2924/16151; H01L 23/315
See application file for complete search history.

(56) References Cited

U.S. PATENT DOCUMENTS

| | | | |
|---|---|---|---|
| 5,910,659 A | 6/1999 | Johnson et al. | |
| 8,698,376 B2* | 4/2014 | Chen ..................... | H03H 3/007 310/309 |
| 9,632,265 B2* | 4/2017 | Nekado ................. | G02B 6/421 |
| 2011/0209815 A1 | 9/2011 | Aono et al. | |
| 2012/0228733 A1 | 9/2012 | Garcia-Blanco et al. | |
| 2015/0158720 A1* | 6/2015 | Lim .................... | B81C 1/00285 257/415 |
| 2016/0343921 A1 | 11/2016 | Stanley et al. | |

* cited by examiner

*Primary Examiner* — Hsien Ming Lee
(74) *Attorney, Agent, or Firm* — Slater Matsil, LLP

(57) ABSTRACT

The present disclosure relates to an apparatus having a substrate arrangement with a first circuit arrangement that heats up during operation and a second circuit arrangement that is integrated into a substrate material of the substrate arrangement. Further, the apparatus has a cavity structure that is arranged between the first and the second circuit arrangement, said cavity structure being formed in the substrate material and having a pressure that is lower than an ambient atmospheric pressure. The present disclosure further relates to a method for producing such an apparatus (10).

29 Claims, 9 Drawing Sheets

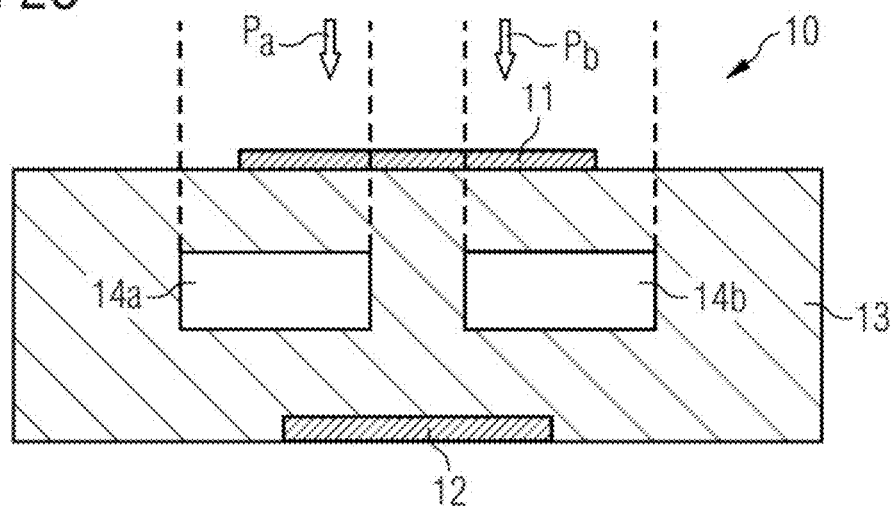
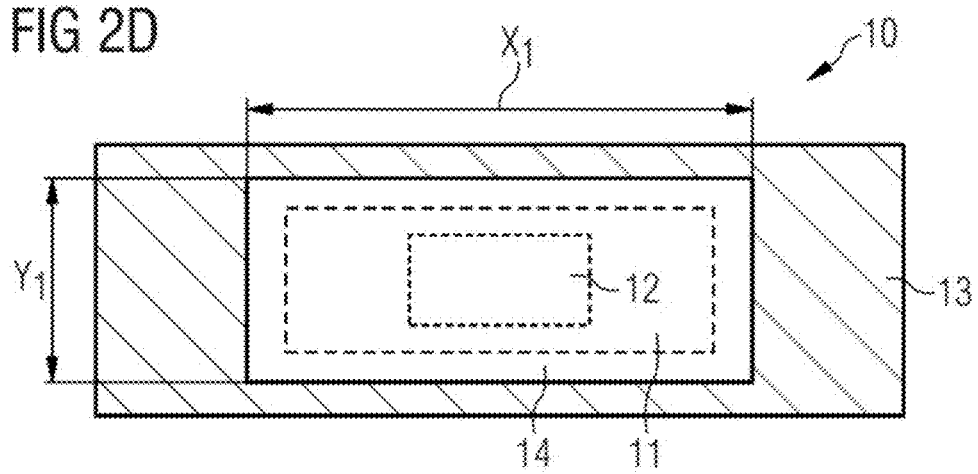

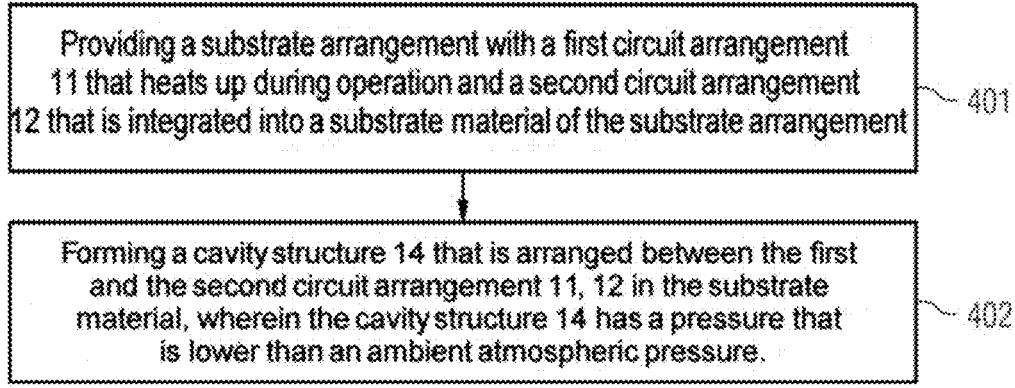
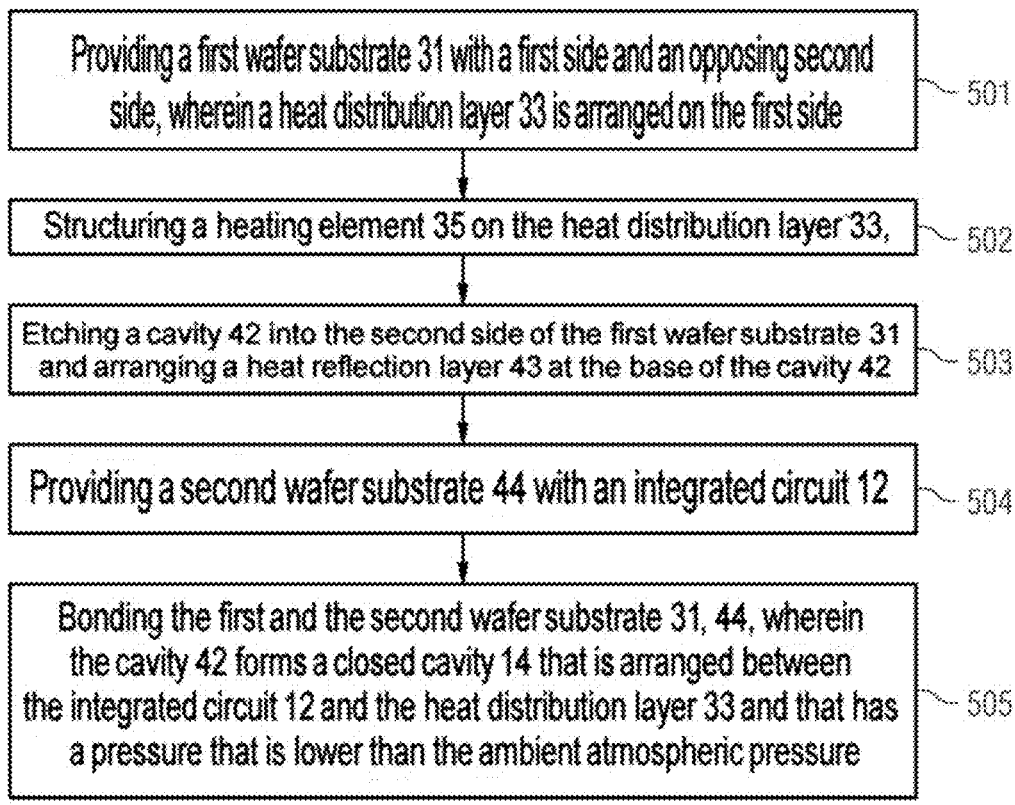

US 10,442,682 B2

APPARATUS HAVING A CAVITY STRUCTURE AND METHOD FOR PRODUCING SAME

This application claims the benefit of German Application No. 102017204817.4, filed on Mar. 22, 2017, which application is hereby incorporated herein by reference in its entirety.

TECHNICAL FIELD

The present disclosure relates to an apparatus having a cavity structure and a method for producing same.

BACKGROUND

In the case of integrated circuits, such as e.g. in MEMS (micro-electromechanical systems), the size and the height and also the power loss play a great role, in particular if the chip is intended to be implemented in mobile appliances such as smartphones, for example. Moreover, much attention should be directed to the costs of MEMS solutions.

SUMMARY

One aspect of the present disclosure relates to an apparatus having a substrate arrangement with a first circuit arrangement that heats up during operation and a second circuit arrangement that is integrated into a substrate material of the substrate arrangement, and a cavity structure that is arranged between the first and the second circuit arrangement, said cavity structure being formed in the substrate material and having a pressure that is lower than an ambient atmospheric pressure.

A further aspect of the present disclosure relates to a method in which a substrate arrangement with a first circuit arrangement that heats up during operation and a second circuit arrangement that is integrated into a substrate material of the substrate arrangement is provided. Moreover, a cavity structure that is arranged between the first and the second circuit arrangement is formed in the substrate material according to this method, wherein the cavity structure has a pressure that is lower than an ambient atmospheric pressure.

BRIEF DESCRIPTION OF THE DRAWINGS

Exemplary embodiments of the present disclosure are illustrated in the drawing and will be explained below. In the drawing:

FIG. 2C shows a lateral sectional view of a further exemplary embodiment of an apparatus according to the present disclosure;

FIG. 2D shows a plan view of an exemplary embodiment of an apparatus according to the present disclosure;

FIG. 4 shows a schematic block diagram of an exemplary embodiment for a method according to the present disclosure; and FIG. 5 shows a schematic block diagram of a further exemplary embodiment for a method according to the present disclosure.

DETAILED DESCRIPTION OF ILLUSTRATIVE EMBODIMENTS

Some exemplary embodiments are described in more detail below with reference to the figures, with elements that have the same or a similar function being provided with the same reference sign.

Some embodiments of the present invention are directed to an integrated circuit arrangement and a circuit arrangement that heat up during operation and are implemented in a common package. In some embodiments, this package has a small size, low height and low cost for use, for example, in a mobile appliance. In some embodiments, the size of the package is minimized, and costs and power loss during application are reduced. Embodiments may be directed to a structure and a method for an integrated IR emitter, filter and ASIC with a reduced energy consumption and a reduced volume. Advantages of embodiments of the present invention include small size, lower power loss and low heat emission, which make such embodiments suitable for mobile appliances.

Figure 1:
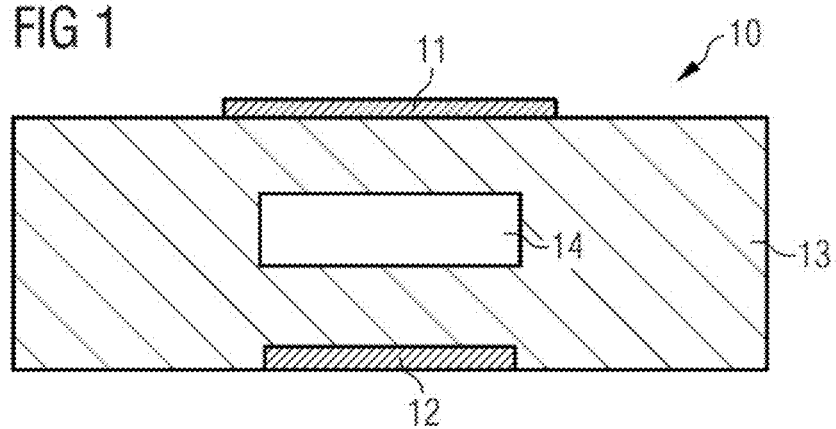
FIG. 1 shows a lateral sectional view of an exemplary embodiment of an apparatus according to the present disclosure.

FIG. 1 shows an apparatus 10 according to one exemplary embodiment. The apparatus has, inter alia, a substrate arrangement 13. The substrate arrangement 13 may have a single substrate, a plurality of substrates or one or more partial substrate arrangements.

The substrate arrangement 13 has a first circuit arrangement 11 that heats up during operation and a second circuit arrangement 12. The second circuit arrangement 12 is integrated in a substrate material of the substrate arrangement 13. Here, this may be an integrated circuit, abbreviated IC. By way of example, the second circuit arrangement 12 can be an ASIC (application-specific integrated circuit).

The first circuit arrangement 11 may likewise be an IC. However, it is also conceivable for the first circuit arrangement 11 to be a non-integrated circuit arrangement that is mounted or structured in, at or on the substrate arrangement 13 by means of known methods, e.g. using SMD (surface mounted device) technology or by means of a structuring method. By way of example, the first circuit arrangement 11 can be a MEMS (micro-electromechanical system) component, e.g. a MEMS heating element or a MEMS microphone.

Moreover, the apparatus 10 has a cavity structure 14 that is formed in the substrate material of the substrate arrangement 13. This cavity structure 14 is arranged between the first and the second circuit arrangement 11, 12. The cavity structure 14 has a lower pressure than an ambient atmospheric pressure.

The ambient atmospheric pressure need not necessarily be the air pressure; instead, this generally is the pressure of a medium surrounding the apparatus 10. The ambient atmospheric pressure can also be referred to as the hydrostatic pressure of the respective medium. This may vary according to position and height. Thus, for example, the standard air pressure at sea level is approximately 1013.25 hPa, i.e. approximately 1 bar.

By way of example, there may be a vacuum in the cavity structure 14, at least to the extent that a vacuum is producible within the scope of what is technically possible. Here, this will usually not be able to be an absolute or one hundred percent vacuum in reality. Therefore, the conventional technological definition for the term vacuum is used in the present disclosure, namely that this is a space that is virtually completely emptied of air.

According to one exemplary embodiment, the pressure in the cavity structure can be less than 10% or less than 1% of the ambient atmospheric pressure. Thus, there is negative pressure in the cavity structure 14 in relation to the ambient atmospheric pressure. By way of example, in the case of the aforementioned standard air pressure at sea level, the negative pressure in the cavity structure 14 is less than approximately 101.33 hPa, i.e. approximately 0.1 bar, or less than approximately 10.13 hPa, i.e. approximately 0.01 bar.

If the pressure in the cavity structure 14 drops below 0.3 bar or 300 mbar and if more and more molecules are removed from the cavity structure 14, a low vacuum is obtained, followed by a medium vacuum, a high vacuum and, lastly, an ultra-high vacuum (like in outer space). In this technical sense, a negative pressure with the low pressures specified in the present disclosure may be denoted by the generic term vacuum.

FIGS. 2A, 2B, 2C and 2D show further examples of an apparatus 10 according to the present disclosure and elucidate conceivable relative spatial orientations of the first circuit arrangement 11, the second circuit arrangement 12, and the cavity structure 14 relative to one another.

Figure 2A:
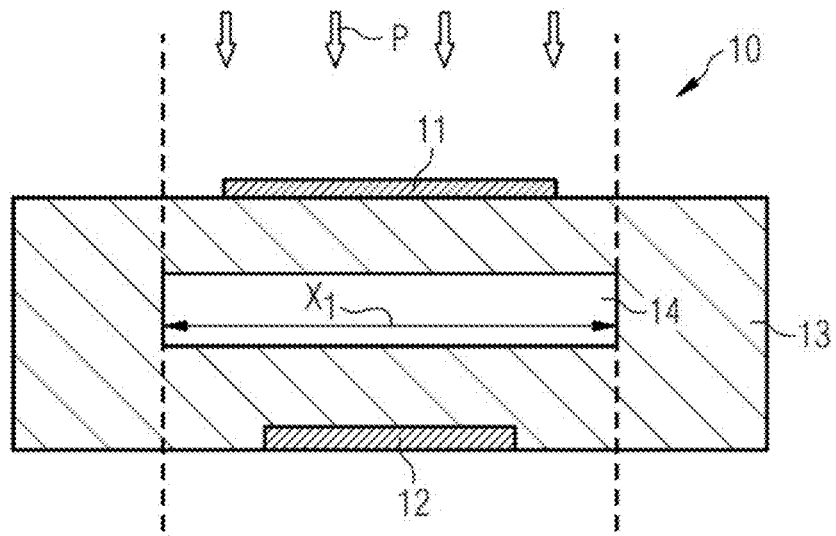
FIG. 2A shows a lateral sectional view of a further exemplary embodiment of an apparatus according to the present disclosure.

By way of example, FIG. 2A shows an exemplary embodiment according to which the cavity structure 14 extends between the two circuit arrangements 11, 12 in a lateral direction $X_1$ and at least the first circuit arrangement 11 or the second circuit arrangement 12 is arranged completely within a projection P of the cavity structure 14 perpendicular to this lateral direction of extent $X_1$.

This projection P is intended to be explained in more detail with reference to FIG. 2D. This is a plan view of the apparatus 10. It is possible to see the lateral dimensions of the substrate arrangement 13, of the first circuit arrangement 11, of the second circuit arrangement 12, and of the cavity structure 14.

As mentioned at the outset, the cavity structure 14 extends in a lateral direction of extent X1. As is identifiable in FIG. 2D, the cavity structure 14 may moreover extend in a second lateral direction of extent Y1 that is identifiable here. Consequently, the plan view illustrated in FIG. 2D shows the projection P of the cavity structure 14 perpendicular to the lateral directions of extent $X_1$, $Y_1$.

As may be identified further, the first circuit arrangement 11 and the second circuit arrangement 12 may lie completely within this projection P of the cavity structure 14 in this case.

By way of example, only the second circuit arrangement 12 lies completely within the projection P of the cavity structure 14 in FIG. 1 and the first circuit arrangement 11 only lays within the projection P of the cavity structure 14 in portions. However, the other way round is likewise conceivable.

Figure 2B:
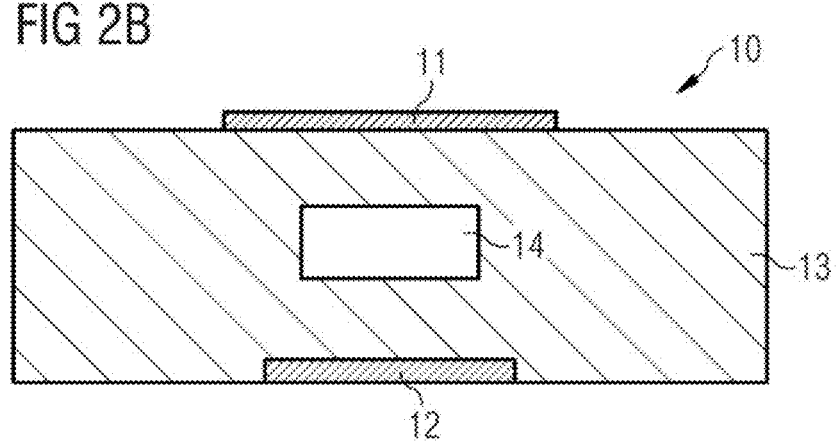
FIG. 2B shows a lateral sectional view of a further exemplary embodiment of an apparatus according to the present disclosure.

In FIG. 2B, both the first and the second circuit arrangement 11, 12 can lie within the projection P of the cavity structure 14 in portions.

FIG. 2C shows an exemplary embodiment with two cavity structures 14a, 14b, wherein both the first and the second circuit arrangement 11, 12 are respectively able to lie within the projection $P_a$, $P_b$ of at least one of the two cavity structures 14a, 14b in portions. Naturally, the same likewise applies in respect of the overlap regions if only one of the two imaged cavity structures 14a, 14b were present.

FIGS. 3A to 3L show individual process steps that can be carried out in the imaged sequence, or else in a sequence that deviates therefrom, in order to obtain an aforementioned apparatus 10. One or more of the method steps imaged in FIGS. 3A to 3K may be optional.

Figure 3A:
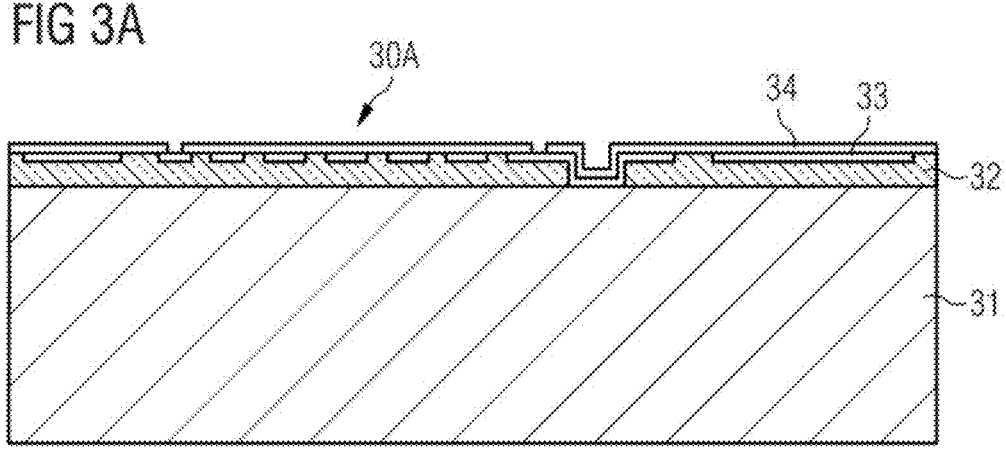
FIG. 3A shows a first step of an exemplary embodiment of a method for producing an apparatus according to this disclosure.

A first substrate 31 is provided in FIG. 3A. The substrate 31 may be a wafer substrate which, after the processing has been completed, is diced into individual chips. By way of example, the substrate or wafer substrate 31 can be a silicon substrate.

A first layer 32, for example a passivation and/or etch stop layer, e.g. an oxide layer 32, is deposited on the upper or first surface 30A, as imaged in FIG. 3A, of the wafer substrate 31. A further layer 33 that is embodied to distribute heat or thermal radiation is deposited on the oxide layer 32. By way of example, this layer 33 can be a polysilicon layer.

A further layer 34 is deposited on the two layers 32, 33. This may be a nitride layer. The nitride layer 34 may be embodied to form a membrane that is capable of vibrations, as described in more detail below.

Figure 3B:
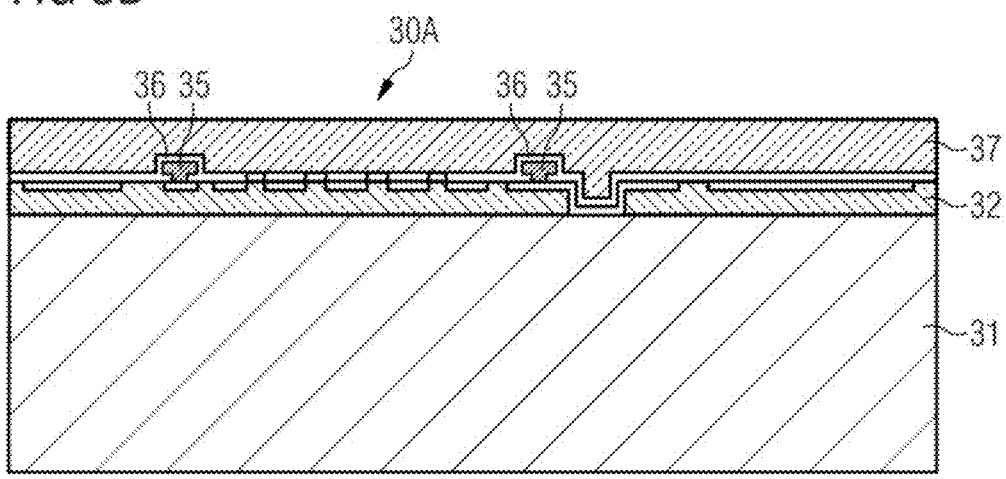
FIG. 3B shows a second step of this method for producing an apparatus according to the present disclosure.

As shown in FIG. 3B, it is then possible to structure a heating element 35. The heating element 35 may have a metal, preferably with a high thermal conductivity, such as platinum, for example. The heating element 35 may extend along the first side or surface 30A of the wafer substrate 31, for example in a meandering manner.

The heating element 35 may be covered by a further layer 36, for example a further nitride layer 36. Moreover, it is possible to deposit a further passivation and/or etch stop layer 37, for example a further oxide layer 37, on the structured wafer substrate 31.

Figure 3C:
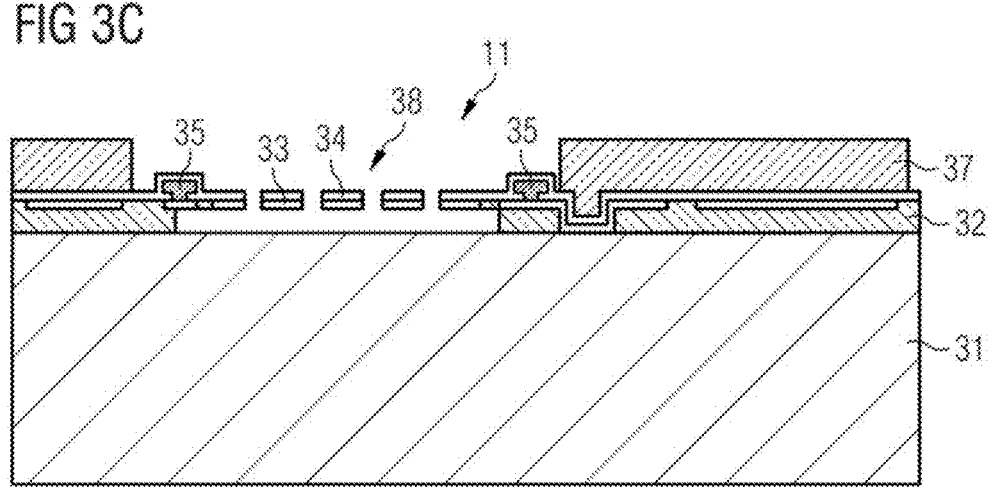
FIG. 3C shows a third step of this method for producing an apparatus according to the present disclosure.

As shown in FIG. 3C, an oxide removal process can be used to remove the oxide layers 32, 37, at least in the region of the heating elements 35 and the portions of the nitride and polysilicon layers 33, 34 arranged therebetween. To this end, use can be made of conventional dry chemical or wet chemical etching methods.

The first circuit arrangement 11 that heats up during operation has at least the aforementioned heating elements 35. As described in more detail below, the heating elements 35 can be contacted electrically such that the heating elements 35 heat up as a consequence thereof. The heat arising in the process can be output in the form of infrared radiation (IR radiation), for example.

The heat produced by the first circuit arrangement 11 or the heating elements 35 can be transferred to at least one of the layers 33, 34 that are thermally coupled to the heating elements 35.

Here, the polysilicon layer 33 can be embodied as a heat spreader layer, for example. Consequently, this heat spreader layer 33 may also be referred to as a heat distribution element 33. This heat distribution element 33 is embodied to distribute the heat produced by the first circuit arrangement 11 over the entire surface of the heat distribution apparatus 33 in an approximately uniform manner.

Together with the heat distribution element 33, the heating elements 35 can form an IR emitter. Consequently, the first circuit arrangement 11 has an IR emitter 33, 35.

The nitride layer 34 arranged above the heat distribution element 33 may be embodied as a membrane that reacts to air vibrations, said membrane being usable as a microphone membrane, for example.

Thus, using the optional steps described up until now, it is possible to obtain a substrate arrangement 31 with a first circuit arrangement 11 that heats up during operation. This substrate arrangement 31 that is imaged in FIG. 3C may also be referred to as a emitter wafer.

Figure 3D:
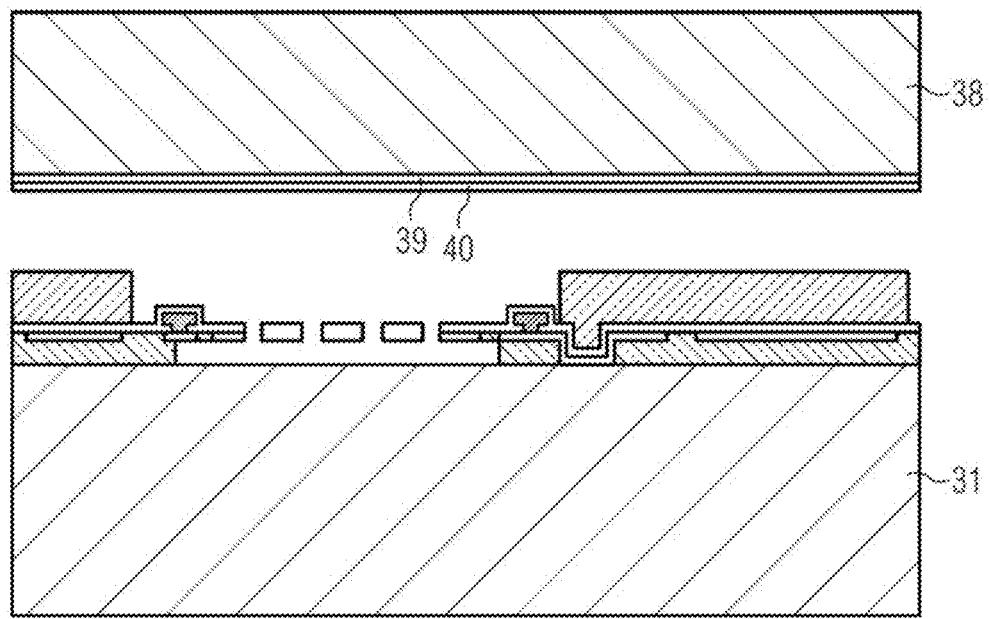
FIG. 3D shows a fourth step of this method for producing an apparatus according to the present disclosure.

In FIG. 3D, a second substrate 38 or a second wafer substrate 38, for example a silicon wafer substrate 38, is provided. The second wafer substrate 38 may have a coating 39 on the side facing the processed first wafer substrate 31, said coating being embodied to filter light of a specific wavelength. By way of example, this may be a layer 39 that passes light in the infrared wavelength range (IR).

A further coating 40 may be arranged in the IR filter layer 39. By way of example, this may be an SOG (spin-on-glass) layer for making the surface of the second wafer substrate 38 planar.

Figure 3E:
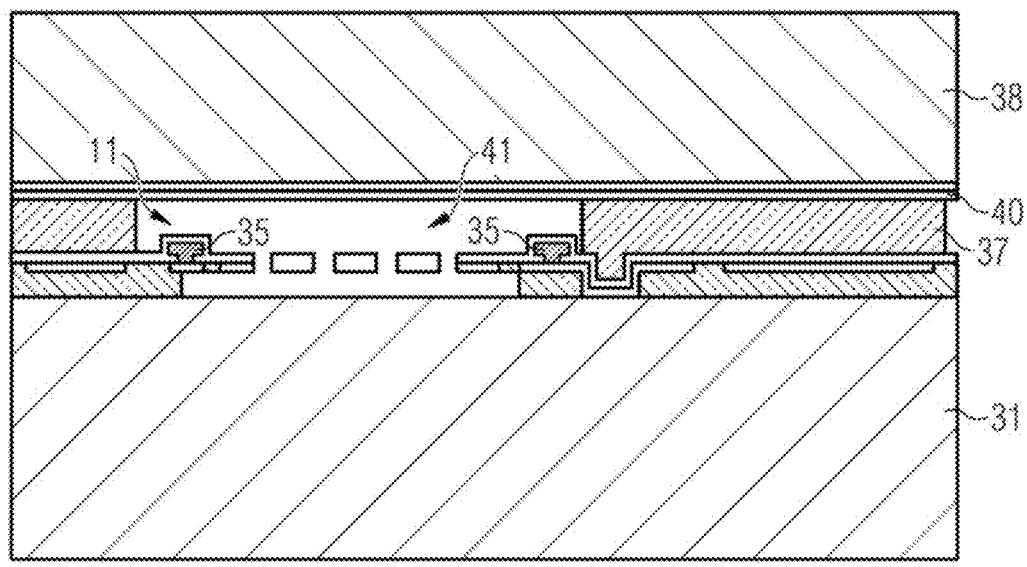
FIG. 3E shows a fifth step of this method for producing an apparatus according to the present disclosure.

As is visible in FIG. 3E, the two wafer substrates 31, 38 then can be bonded to one another. To this end, the oxide layer 37 of the first wafer substrate 31 is connected to the SOG layer 40 of the second wafer substrate 38. Here, a cavity structure 41 is formed in a region between the heating elements 35.

A vacuum bonding method can be used for bonding the two wafer substrates 31, 38 such that a vacuum is formed in the cavity structure 41.

Consequently, a substrate arrangement consisting of two substrates 31, 38 and having a first circuit arrangement 11 that heats up during operation is obtained.

Figure 3F:
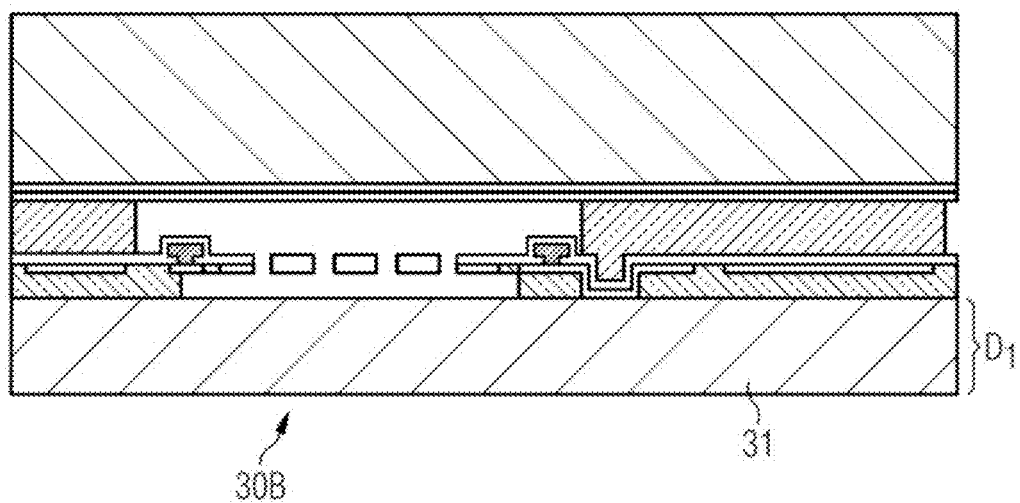
FIG. 3F shows a sixth step of this method for producing an apparatus according to the present disclosure.

As shown in FIG. 3F, the first wafer substrate 31 can be optionally thinned to a desired strength or thickness D1, for example 50 μm or less. Here, it is possible to thin the second side 30B or the lower side of the wafer substrate 31, for example by means of polishing, grinding, etc.

Figure 3G:
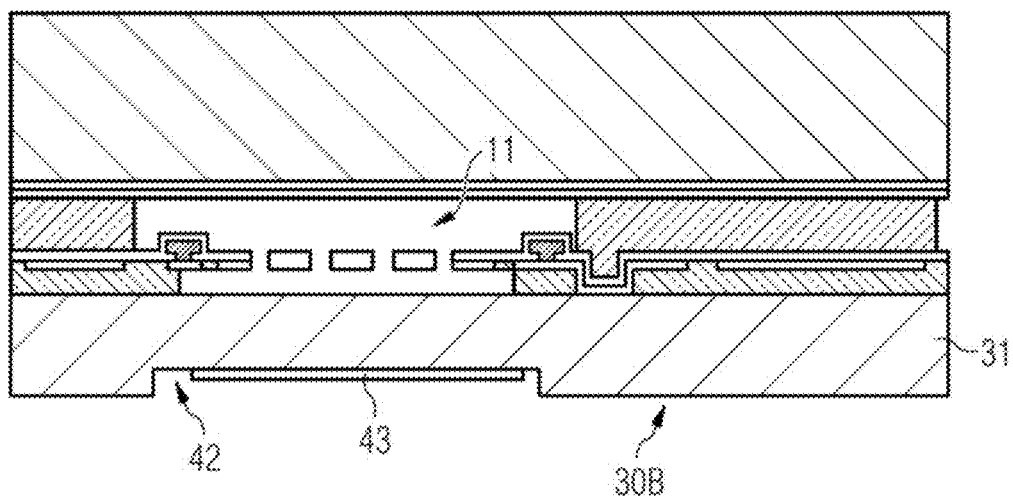
FIG. 3G shows a seventh step of this method for producing an apparatus according to the present disclosure.

As shown in FIG. 3G, a cavity 42 can be formed in the first wafer substrate 31 on the lower side 30B, facing away from the first circuit arrangement 11, of the first wafer substrate 31. By way of example, this cavity 42 can be formed by means of conventional structuring methods.

Optionally, a reflection arrangement 43 for reflecting thermal radiation emitted by the first circuit arrangement 11 may be provided in the cavity 42. This reflection arrangement 43 can be arranged at the base of the cavity 42, i.e. on a surface region of the cavity 42 that faces the first circuit arrangement 11. The reflection arrangement 43 can be deposited in the cavity 42 as a layer, for example as a metal layer, and can be structured accordingly.

It is conceivable for the reflection arrangement 43 to have approximately the same lateral dimensions as the first circuit arrangement 11 and/or the second circuit arrangement 12.

Moreover, the reflection arrangement 43 may be arranged completely within a projection of the cavity 42 or completely within a projection of the first and/or second circuit arrangement 11, 12 perpendicular to (see FIG. 2D) the lateral direction of extent of the cavity 42 or the circuit arrangements 11, 12.

Figure 3H:
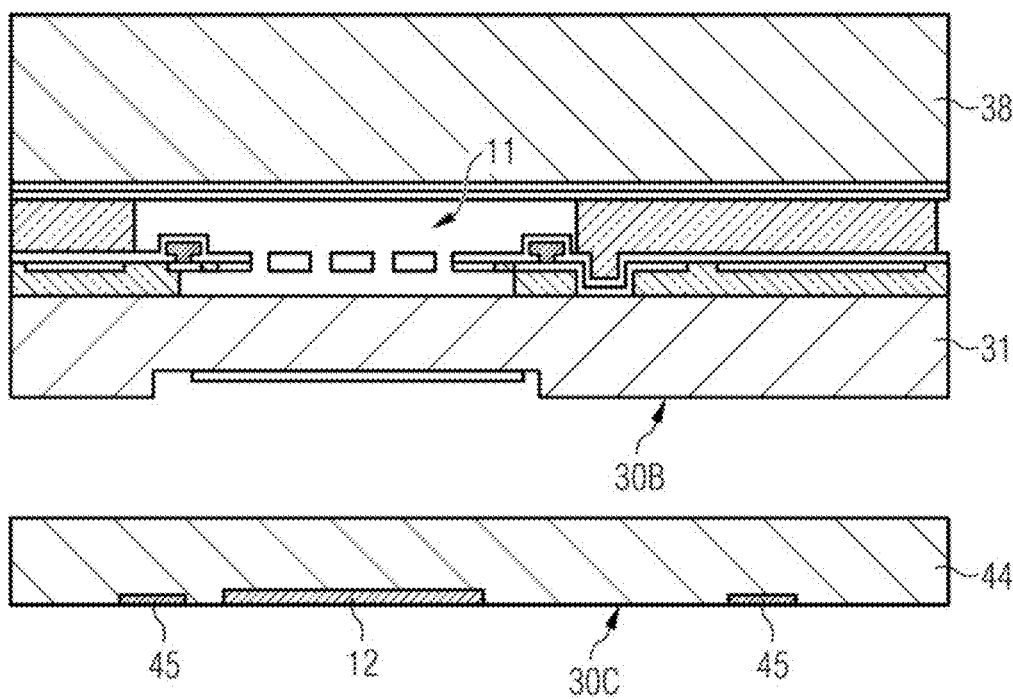
FIG. 3H shows an eighth step of this method for producing an apparatus according to the present disclosure.

As shown in FIG. 3H, provision can be made of a third substrate or wafer substrate 44, e.g. a silicon wafer substrate 44. A second circuit arrangement 12 can be integrated in this third wafer substrate 44. In the example imaged here, the second circuit arrangement 12 can be an integrated ASIC (application-specific integrated circuit). This ASIC 12 can be arranged in rearward fashion at the second side or lower side 30B of the first wafer substrate 31. Consequently, the ASIC 12 can also be referred to as a flipped ASIC.

Thus, the third wafer substrate 44 having the second circuit arrangement 12 can be arranged or bonded on a side 30B of the first wafer substrate 31 that is opposite to the first circuit arrangement 11. The ASIC 12 itself can be integrated or structured on the side 30C of the third wafer substrate 44 that lies opposite the bond side or the first wafer substrate 31.

Optionally, electrical connector contact areas 45, e.g. bond pads 45, for electrical contacting of the ASIC 12 can also be provided on precisely this side 30C of the third wafer substrate 44. Consequently, the entire apparatus 10 can later be assembled on a PCB or the like, for example, by means of flip-chip assembly technology.

Figure 3I:
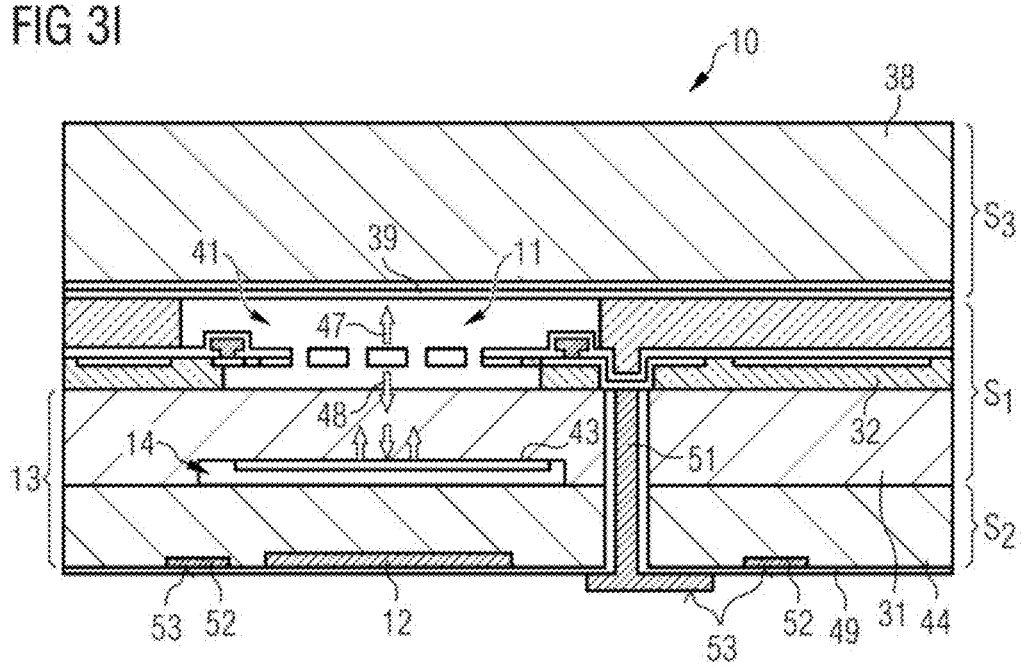
FIG. 3I shows a ninth step of this method for producing an apparatus according to the present disclosure.

The result of bonding the first wafer substrate 31 to the third wafer substrate 44 is imaged in FIG. 3I.

In FIG. 3I, it is possible to identify that a closed cavity structure 14 is formed by bonding the first wafer substrate 31 to the third wafer substrate 44. The first wafer substrate 31 and the third wafer substrate 44 can be bonded to one another using a vacuum bonding method, and so a vacuum within the meaning of the present disclosure is present in the cavity structure 14.

Using the partly optional steps described above, it is thus possible to obtain an apparatus 10 with a substrate arrangement 13, with this substrate arrangement 13 having a first circuit arrangement 11 that heats up during operation and a second circuit arrangement 12 that is integrated into a substrate material of the substrate arrangement 13.

In this exemplary embodiment, the substrate arrangement 13 has at least the emitter wafer, i.e. the above-described first wafer substrate 31, and the ASIC wafer, i.e. the above-described third wafer substrate 44. Optionally, as imaged here in FIG. 3I, the overall apparatus 10 may also still have a filter substrate, i.e. the above-described second wafer substrate 38, in addition to this substrate arrangement 13.

The substrate arrangement 13 imaged in FIG. 3I has two partial substrate arrangements $S_1$, $S_2$ that are stacked over one another in this exemplary embodiment. In this exemplary embodiment, the first partial substrate arrangement $S_1$ is represented by the above-described first wafer substrate 31. The first partial substrate arrangement $S_1$ has the first circuit arrangement 11. In this exemplary embodiment, the second partial substrate arrangement $S_2$ is represented by the third wafer substrate 44 that has the ASIC 12.

The apparatus 10 has a cavity structure 14 arranged between the first and the second circuit arrangement 11, 12, said cavity structure being formed in the substrate material of the substrate arrangement 13 and having a lower pressure than an ambient atmospheric pressure.

As already mentioned previously, the hollow structure 14 is formed as a closed-off recess in at least one of the two partial substrate arrangements $S_1$, $S_2$. In the above-described method, this recess 14 was formed by the cavity 42 that was formed in the first wafer substrate 31. However, it is just as easily conceivable for such a cavity 42 to be formed at a corresponding place in the third wafer substrate 44, or in both the first and the third wafer substrate 31, 44.

As already described previously with reference to FIG. 3C, the first circuit arrangement 11 may have one or more heating elements 35. The layer 33 can be thermally coupled to the heating element 35 and can serve as a layer that spreads heat or emits heat, said layer being able to form an IR emitter together with heating elements 35.

Thus, the heat emitted by the first circuit arrangement 11 can be emitted, for example, in the form of electromagnetic radiation and, in particular, in the form of infrared radiation. The electromagnetic radiation emitted by the first circuit arrangement 11 has a principal emission direction 47 in this case. As imaged, the principal emission direction 47 may be directed in the direction of the second wafer substrate 38, wherein the emitted thermal radiation is able to be output coupled into the surroundings through the second wafer substrate 38. A main component, i.e. more than 50%, of the emitted thermal radiation can be emitted in this principal emission direction 47.

Moreover, the electromagnetic radiation emitted by the first circuit arrangement 11 may have a secondary emission direction 48. This secondary emission direction 48 differs from the principal emission direction 47. In this exemplary embodiment, the secondary emission direction 48 is directed in the direction of the cavity structure 14, and consequently opposite to the principal emission direction 47.

The electromagnetic radiation emitted into the secondary emission direction 48 can be reflected back into the principal emission direction 47 at the above-described reflection arrangement 43.

As already described above with reference to FIG. 3D, the apparatus 10 has an optical filter 39. In the exemplary embodiment described here, this may relate to the layer 39 that was described at the outset, said layer, for example, being able to be embodied as an IR filter layer.

The optical filter 39 may be arranged downstream of the first circuit arrangement 11 in the principal emission direction 47. Moreover, the second cavity structure 41, mentioned above in relation to FIG. 3E, may be formed between the first circuit arrangement 11 and the optical filter 39. Compared to an ambient atmospheric pressure, this second cavity structure 41 may have a lower pressure.

According to one exemplary embodiment, the pressure in the second cavity structure 41 is less than 10% or less than 1% of the ambient atmospheric pressure. The second cavity structure 41 can have a vacuum within the meaning of the present disclosure.

According to conceivable exemplary embodiments, the optical filter 39 may have a monolithic embodiment with the second wafer substrate 38 or with the third partial substrate arrangement $S_3$. As a reminder, the third partial substrate arrangement $S_3$ can have the second wafer substrate 38 and, optionally, further substrates (not illustrated here for simplification purposes).

According to the exemplary embodiment imaged in FIG. 3I, the optical filter 39 can be arranged at the third partial substrate arrangement $S_3$, wherein this third partial substrate arrangement $S_3$ can be connected to the substrate arrangement 13 having the first and the second partial substrate arrangements $S_1$, $S_2$.

Consequently, the third partial substrate arrangement $S_3$ can also be referred to as a filter wafer.

As furthermore shown in FIG. 3I, the substrate arrangement 13 can have at least one electrical connector 51 for contacting the first circuit arrangement 11 and at least one electrical connector 52 for contacting the second circuit arrangement 12.

Contact areas 53 of the electrical connectors 51, 52 can be arranged at a portion of the substrate arrangement having the second circuit arrangement 12. In the present exemplary embodiment, the contact areas 53 of the electrical connectors 51, 52 are arranged at the second partial substrate arrangement $S_2$ that has the ASIC 12. As a reminder, the second substrate arrangement $S_2$ can have the third wafer substrate 44 and optionally further substrates (not illustrated here for simplification purposes).

In the step shown in FIG. 3I, the contact areas 53 are covered by a passivation layer 49, e.g. an oxide layer.

Figure 3J:
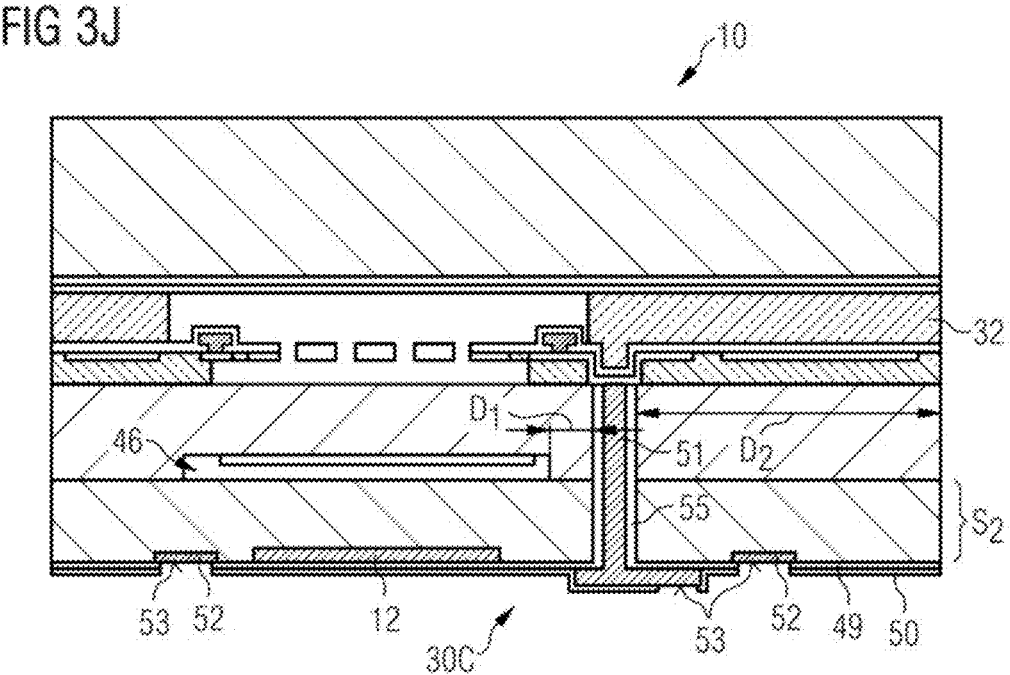
FIG. 3J shows a tenth step of this method for producing an apparatus according to the present disclosure.

FIG. 3J shows a further conceivable process step. Here, a passivation layer 50, e.g. a nitride layer, was deposited on the oxide layer 49 and the contact areas 53 of the electrical connectors 51, 52 for the first and the second circuit arrangement 11, 12 were exposed, for example by means of plasma etching or using other suitable methods.

Here, the electrical connector 51 of the first circuit arrangement 11 is formed as a TSV (through silicon via) 55 in an exemplary manner, said TSV extending through the substrate arrangement 13.

To this end, such a TSV 55 can be etched, for example, from the rear side 30C, facing away from the cavity structure 14, of the second partial substrate arrangement $S_2$ in the direction of the first circuit arrangement 11, to be precise as far as the oxide layer 32 that acts as an etch stop here. Subsequently, the TSV 55 is processed in the form of an oxide spacer and the TSV 55 can be filled with a barrier layer and with a thermally and/or electrically conductive material. By way of example, copper can be used to fill the TSV 55.

According to conceivable exemplary embodiments, the apparatus 10 can have a multiplicity of TSVs 55 (not explicitly imaged here) that are arranged laterally around the cavity structure 14 and filled with a thermally and/or electrically conductive material.

Here, the plurality of TSVs 55 may have a distance $D_1$ from the cavity structure 14 that is less than a distance $D_2$ to a lateral or sideward outer side of the substrate arrangement. Consequently, the TSVs 55 can be arranged as close as possible to the cavity structure 14.

The above-described process steps can be carried out on an individual chip or at a wafer level in order to save costs. In the latter case, a wafer stack with a multiplicity of the above-described apparatuses 10 is present at the end.

Figure 3K:
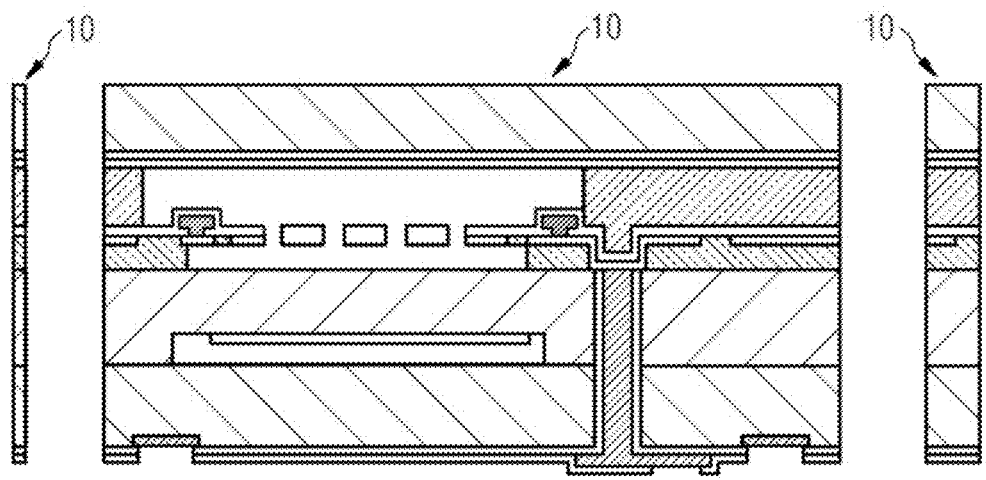
FIG. 3K shows an eleventh step of this method for producing an apparatus according to the present disclosure.

As shown in FIG. 3K, this wafer stack can be diced. In the process, a multiplicity of individual packages 10 or individual apparatuses 10 according to one exemplary embodiment are obtained.

Optionally, a so-called RDL (redistribution layer) can be implemented before dicing the packages 10 in order to contact the TSVs 55 with the last metal of the ASIC 12.

Figure 3L:
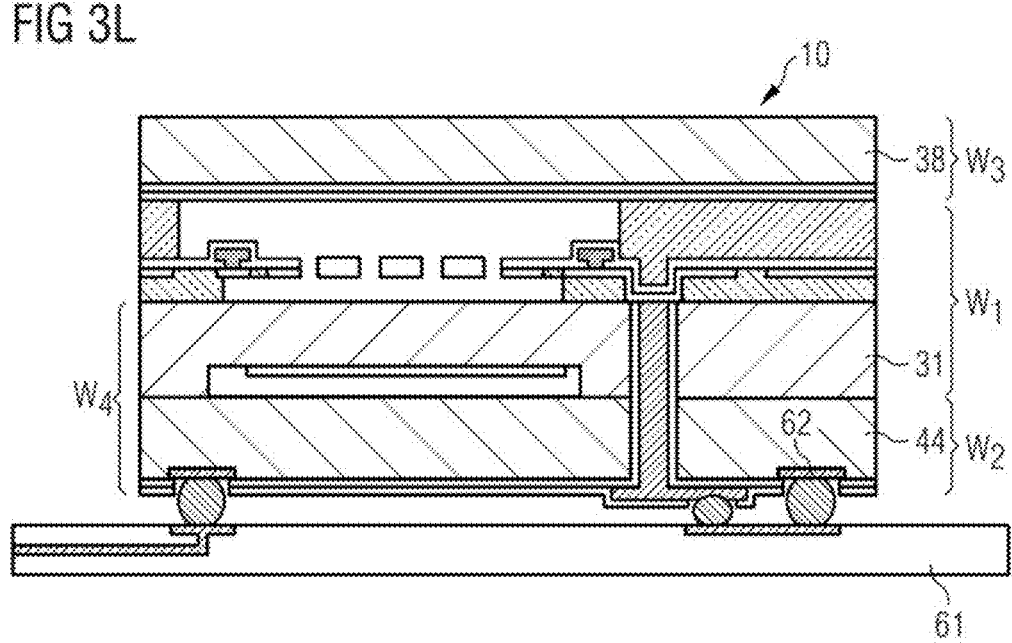
FIG. 3L shows a twelfth step of this method for producing an apparatus according to the present disclosure.

In FIG. 3L, a diced package 10 or diced apparatus 10 that is arranged on a substrate 61 is imaged. By way of example, this substrate 61 can be a printed circuit board PCB or a laminate with a known construction. Here, for example using so-called bump technology, the apparatus 10 can be fastened by means of micro-pillar technology or by means of RDLs in an eWLB (embedded wafer level ball grid array). To this end, use can be made of so-called bumps or pillars 62.

As described above, the apparatus 10 can have a plurality of partial substrate arrangements $S_1$, $S_2$, $S_3$, which, in turn, may have one or more individual substrates 31, 38, 44. The first partial substrate arrangement $S_1$ can have a thickness $W_1$, which is approximately 50 μm. The second partial substrate arrangement $S_2$ can have a thickness $W_2$, which is approximately 65 μm. The third partial substrate arrangement $S_3$ can have a thickness $W_3$, which is approximately 35 μm. Together, the first and the second substrate 31, 44 can have a thickness $W_4$ of approximately 110 vim.

FIG. 4 shows, in summary, a block diagram of an exemplary embodiment for a method according to the present disclosure.

In block 401, a substrate arrangement 13 with a first circuit arrangement 11 that heats up during operation and a second circuit arrangement 12 that is integrated into a substrate material of the substrate arrangement 13 is provided.

In block 402, a cavity structure 14 that is arranged between the first and the second circuit arrangement 11, 12 is formed in the substrate material, wherein the cavity structure 14 has a pressure that is lower than an ambient atmospheric pressure.

FIG. 5 shows, in summary, a block diagram of a further exemplary embodiment for a method according to the present disclosure.

In block 501, a first wafer substrate 31 with a first side 30A and an opposing second side 30B is provided, wherein a heat distribution layer 33 is arranged on the first side 30A.

In block 502, a heating element 35 is structured on the heat distribution layer 33.

In block 503, a cavity 42 is etched into the second side 30B of the first wafer substrate 31 and a heat reflection layer 43 is arranged at the base of the cavity 14.

In block 504, a second wafer substrate 44 with an integrated circuit 12 is provided.

In block 505, the first and the second wafer substrate 31, 44 are bonded, wherein the cavity 42 forms a closed cavity 14 that is arranged between the integrated circuit 12 and the heat distribution layer 33 and that has a pressure that is lower than the ambient atmospheric pressure.

Now that the structural features have been described, the functionality is intended to be described with reference to FIG. 3L.

The apparatus 10 disclosed here can be used as a photoacoustic sensor, for example. The first circuit arrangement 11 can have a heating element 35 for emitting thermal radiation. The second circuit arrangement 12 may be an ASIC for controlling the heating element 35.

During operation, the heating element 35 may produce temperatures of 300° C. to 800° C. However, the ASIC 12 lying therebelow should only heat up by a few 10° C. By way of example, the ASIC should not be heated to more than 65° C. However, the distance between the heating element 35 and the ASIC 12 within the apparatus 10 is only a few micrometer. Consequently, it is a challenge to thermally decouple the ASIC 12 from the heating element 35 to the greatest possible extent.

In the apparatus 10, this is achieved, inter alia, by the cavity structure 14, with negative pressure and, in particular, a vacuum being found in the cavity structure 14. Since the vacuum conducts the heat output by the heating element 35 poorly between the heating element 35 and the ASIC 12, few thermal losses are produced here. That is to say, only a very small part of the emitted heat is guided into the surrounding structures within the cavity structure 14. Thermal radiation is the dominating effect here in relation to thermal conduction.

A reflection arrangement 43 optionally present in the cavity structure 14 may additionally keep the thermal radiation away from the ASIC 12. To this end, the reflection arrangement 43 is arranged between the ASIC 12 and the heating element 35. Expressed more generally, the reflection arrangement 43 is arranged between the first circuit arrangement 11 and the second circuit arrangement 12.

The heating element 35 and the heat-emitting layer 33 that is thermally coupled to the heating element 35 can together form a heat distribution element 33, 35. The heat distribution element may be an IR emitter, for example. The IR emitter 33, 35 can emit in at least one of at least two directions, i.e. in the direction of the cavity structure 14 and in the direction of the IR filter 39.

The IR emitter 33, 35 may be situated in a second cavity structure 41, in which there likewise is negative pressure or a vacuum. This vacuum likewise serves the above-described purpose, with thermal radiation dominating over thermal conduction. Consequently, the IR emitter 33, 35 emits just as well as without a vacuum. However, the thermal radiation can propagate in a virtually unimpeded fashion in the vacuum. Consequently, the vacuum avoids an unwanted heating of the surrounding structures.

The upshot is that a desired photoacoustic effect clearly dominates over an unwanted thermoacoustic effect in an apparatus 10 according to the present disclosure.

The TSVs 55 that are filled with thermally conductive material also serve to improve the protection of the ASIC 12 from excessive heating. Heat that is emitted to the emitter substrate 31 and/or to the ASIC substrate 44, for example via the cavity structure 14, can be received by means of the thermally conductive filling in the TSVs 55 and dissipated to a PCB or the like, for example.

The more TSVs 55 are present and the closer these are arranged to the cavity structure 14, the more heat can be dissipated thereby.

Below, the concept of this disclosure should be summarized again in different words.

In the case of integrated circuits, such as e.g. in MEMS (micro-electromechanical systems), the size and the height and also the power loss play a great role, in particular if the chip is intended to be implemented in mobile appliances such as smartphones, for example. Moreover, much attention should be directed to the costs of MEMS solutions.

In one example of the present disclosure, an IR emitter and an IR filter, for example, should be implemented in a single package 10, to be precise with an additional ASIC 12 and a microphone MEMS chip 11 with the smallest possible size or height and costs.

However, known solutions to this end are too large and therefore not suitable for use in mobile appliances.

The present disclosure offers a solution for minimizing the complete IR emitter/filter/ASIC system while reducing costs at the same time. Moreover, the power loss during application is also simultaneously lowered.

In existing concepts, the IR emitter, the filter, and the ASIC are embodied as separate components that have to be housed individually in a common housing. In some specific solutions, the filter is arranged directly on the emitter, which is typically brought about chip-on-chip.

Existing solutions for e.g. a photoacoustic gas sensor, provide for the IR chip to be embodied with, for example a thin heating membrane, a cavity in the silicon substrate, and, optionally, a ventilation hole. In order to prevent too much heating of the filter chip, a spacer (standoff layer) consisting of SU8 (polymer) is arranged between the two chips, which is embodied chip-by-chip on a chip level.

However, the height of the entire arrangement made of emitter and filter becomes very large in this realization and it may even become too large and/or emit too much heat and power to find use in mobile applications. However, the ASIC is arranged separately below the emitter in all these known applications.

By contrast, an exemplary embodiment of the present disclosure provides for the apparatus 10 and the method to be carried out at a wafer level and use wafer-to-wafer bonding processes in order to save both the structural size and the costs connected therewith. Here, the emitter 33, 35, the filter 39, and the ASIC 12 can be stacked over one another on a wafer-level and manufactured as a complete chip stack 10.

Specifically, exemplary embodiments can provide for a cavity 14 including a heating membrane 33, 34 and a filter 39 to be processed by means of a hermetic sealing bonding process. Bonding may be carried out in vacuo such that the heating element 33, 34, 35 and the filter 39 are in a vacuum.

At a subsequent time during this process, this wafer stack formed thus can be bonded hermetically with the ASIC wafer 44 in vacuo, with a vacuum cavity 14 being enclosed in the emitter wafer 31.

On account of the vacuum in this cavity 14 between the filter 39 and the emitter 33, 34, 35, it is possible to significantly reduce the power losses since thermal conduction is reduced in the vacuum and, instead, thermal radiation is the only dominating effect.

On account of the vacuum between the emitter wafer 31 and the ASIC wafer 44, it is possible to reduce the heating of the ASIC 12 by the emitter 33, 34, 35. By way of example, an electrical connection between the emitter 33, 34, 35 and the ASIC 12 can be realized by means of a through silicon via (TSV) 55.

In this example, the ASIC chip 44 and the emitter chip 31 should have approximately the same size.

Individual steps of a possible exemplary embodiment for a method according to the present disclosure should again be briefly and concisely summarized below, with reference to FIGS. 3A to 3L.

In FIG. 3A, there is preprocessing of a silicon substrate wafer 31 with an oxide layer 32 and a polysilicon heat distribution layer 33. A nitride layer 34 is deposited thereon.

In FIG. 3B, a metallic heating element 35 (e.g. platinum) is structured and covered by means of nitride 36 and oxide 37.

In FIG. 3C, oxide-exposing etching is carried out, to be precise in the region of the heat distributor 33, 34 and of the heating element 35.

In FIG. 3D an additional wafer 38 with an IR filter layer 39 and a spin-on-glass layer 40 is prepared.

In FIG. 3E, both wafers 31, 38 are hermetically bonded in vacuo.

In FIG. 3F, the emitter wafer 31 is thinned to the intended thickness, typically approximately 50 µm.

In FIG. 3G, a cavity 42 is etched into the rear side of the emitter wafer 31 and a reflective metal shielding 43 is deposited and structured in this cavity 42.

In FIG. 3H, the ASIC wafer 44 is provided with bond pads 45.

In FIG. 3I, the emitter/filter wafer 31, 38 and the ASIC wafer 44 are hermetically bonded in vacuo. Subsequently, an oxide 49 is deposited and a TSV 55 is formed (for example, by means of TSV etching with an etch stop at the oxide 32 on the emitter wafer 31). An oxide spacer is formed and the TSV 55 is filled with the barrier and copper, and the copper is structured at the rear side of the wafer 44.

In FIG. 3J, a passivation nitride layer 50 is deposited and the bond pads 52 are exposed by means of plasma etching.

In FIG. 3K, the wafer stack 10 is diced. Optionally, a so-called redistribution layer (RDL) can be implemented prior to dicing in order to connect the TSV 55 to the last metal layer of the ASIC 12 (saving area space).

In FIG. 3L, the chip 10 is placed on a laminate/PCB/eWLB, etc., for example by means of bump technology, micro-pillars 62 or RDL in an eWLB (embedded wafer level ball grid array).

An optionally conceivable solution could provide for the filter 39 to be integrated in monolithic fashion in, at or on the emitter wafer 31 and for the emitter wafer 31 and the ASIC wafer 44 to be bonded in vacuo, as described. Accordingly, it is a feature of this disclosure to stack the emitter wafer 31 and the ASIC wafer 44 at a wafer level and to draw a vacuum between the two stacked wafers/chips.

In conclusion, the apparatus and the method according to the present disclosure offer the following advantages: radiation in vacuo reduces heat conduction heating of the ASIC 12 by the emitter 33, 34, 35 is reduced on account of the vacuum between the two wafers (emitter wafer 31 and ASIC wafer 44) a reduction in the overall system volume in respect of height and area an integration of filter 39, heating system 33, 34, 35, and ASIC 12 at a wafer level reduces costs the chip stack 10 can be arranged on a PCB or similar substrate 61 below further chips, such as e.g. an MEMS microphone, by means of micro-bumps 62 and micro-pillars TSVs 55 filled with a thermally conductive material (e.g. copper) can dissipate heat emitted by the emitter 33, 34, 35 past the ASIC 12 and, for example, into the PCB 61 or a similar substrate.

The present disclosure may have the following aspects: an apparatus (10) having a substrate arrangement with a first circuit arrangement (ii) that heats up during operation and a second circuit arrangement (12) that is integrated into a substrate material of the substrate arrangement, and a cavity structure (14) that is arranged between the first and the second circuit arrangement (11, 12), said cavity structure being formed in the substrate material and having a pressure that is lower than an ambient atmospheric pressure.

The apparatus (10) according to aspect 1, wherein the pressure in the cavity structure (14) is less than 10% or less than 1% of the ambient atmosphere pressure.

The apparatus (10) according to aspect 1, wherein the cavity structure (14) extends in lateral direction ($X_1$, $Y_1$) between the two circuit arrangements (11, 12) and at least the first circuit arrangement (11) or the second circuit arrangement (12) is arranged completely within a projection of the cavity structure (14) perpendicular to this lateral direction of extent ($X_1$, $Y_1$).

The apparatus (10) according to aspect 1, wherein the substrate arrangement has two partial substrate arrangements ($S_1$, $S_2$) that are stacked over one another, wherein a first partial substrate arrangement ($S_1$) has the first circuit arrangement (11) and a second partial substrate arrangement ($S_2$) has the second circuit arrangement (12), and the cavity structure (14) is formed as a sealed recess in at least one of the two partial substrate arrangements ($S_1$, $S_2$).

The apparatus (10) according to aspect 1, wherein the apparatus (10) has a heat distribution element (33) that is coupled to the first circuit arrangement (11) and embodied to distribute the heat produced by the first circuit arrangement (11) approximately uniformly over the entire surface of the heat distribution element (33).

The apparatus (10) according to aspect 1, wherein the first circuit arrangement (11) has an IR emitter (33, 35).

The apparatus (10) according to aspect 1, wherein the apparatus (10) has a reflection arrangement (43) for reflecting thermal radiation emitted by the first circuit arrangement (11), wherein the reflection arrangement (43) is arranged within the cavity structure (14) on a surface region of the cavity structure (14) that faces the first circuit arrangement (11).

The apparatus (10) according to aspect 1, wherein the apparatus (10) has an optical filter (39) that is embodied to filter electromagnetic radiation emitted by the first circuit arrangement (11), wherein the optical filter (39) is arranged downstream of the first circuit arrangement (11) in a principal emission direction (47) of the electromagnetic radiation and wherein a second cavity structure (41) is formed between the first circuit arrangement (11) and the filter (39), said second cavity structure having a lower pressure than an ambient atmospheric pressure.

The apparatus (10) according to aspect 8, wherein the pressure in the second cavity structure (41) is less than 10% or less than 1% of the ambient atmospheric pressure.

The apparatus (10) according to aspect 8, wherein the optical filter (39) has a monolithic embodiment with the substrate arrangement.

The apparatus (10) according to aspect 8, wherein the optical filter (39) is arranged at a third partial substrate arrangement ($S_3$) and this third partial substrate arrangement ($S_3$) is connected to the substrate arrangement.

The apparatus (10) according to aspect 1, wherein the substrate arrangement has at least one electrical connector (51) for contacting the first circuit arrangement (11) and at least one electrical connector (52) for contacting the second circuit arrangement (12), wherein contact areas (53) of the electrical connectors (51, 52) are arranged at a portion of the substrate arrangement having the second circuit arrangement (12).

The apparatus (10) according to aspect 12, wherein a via (55) is formed through the substrate arrangement, said via connecting a contact area (53) of the at least one electrical connector (51) for contacting the first circuit arrangement (11) to the first integrated circuit arrangement (11) in an electrically conductive manner, wherein this via (55) is filled with a thermally and electrically conductive material.

The apparatus (10) according to aspect 13, wherein the apparatus (10) has a multiplicity of vias (55) that are arranged laterally around the cavity structure (14) and filled with a thermally and electrically conductive material.

The apparatus (10) according to aspect 13, wherein a distance ($D_1$) between the via (55) and the cavity structure (14) is less than a distance ($D_2$) between the via (55) and an outer side of the substrate arrangement.

A wafer stack having a multiplicity of apparatuses (10) according to aspect 1.

A method including the following steps: providing a substrate arrangement with a first circuit arrangement (11) that heats up during operation and a second circuit arrangement (12) that is integrated into a substrate material of the substrate arrangement, and forming a cavity structure (14) that is arranged between the first and the second circuit arrangement (11, 12) in the substrate material, wherein the cavity structure (14) has a pressure that is lower than an ambient atmospheric pressure.

The method according to aspect 17, wherein the step of forming the cavity structure (14) contains the pressure in the cavity structure (14) being less than 10% or less than 1% of the ambient atmospheric pressure.

The method according to aspect 17, wherein the step of providing the substrate arrangement contains two partial substrate arrangements ($S_1$, $S_2$) being stacked over one another, wherein a first partial substrate arrangement ($S_1$) has the first circuit arrangement (11) and a second partial substrate arrangement ($S_2$) has the second circuit arrangement (12), and wherein the step of forming the cavity structure (14) contains the cavity structure (14) being formed as a sealed recess (42) in at least one of the two partial substrate arrangements ($S_1$, $S_2$).

The method according to aspect 19, wherein the first partial substrate arrangement ($S_1$) and the second partial substrate arrangement ($S_2$) are connected to one another using a vacuum bonding method.

The method according to aspect 17, wherein a reflection arrangement (43) for reflecting thermal radiation emitted by the first circuit arrangement (11) is provided, wherein the reflection arrangement (43) is arranged within the cavity structure (14) at a surface region of the cavity structure (14) that faces the first circuit arrangement (11).

The method according to aspect 17, including providing an optical filter (39) that is embodied to filter electromagnetic radiation emitted by the first circuit arrangement (11), wherein the optical filter (39) is arranged downstream of the first circuit arrangement (11) in a principal emission direction (47) of the electromagnetic radiation, and forming a second cavity structure (41) between the first circuit arrangement (11) and the filter (39), wherein the second cavity structure (41) has a lower pressure than the ambient atmospheric pressure.

The method according to aspect 22, wherein the step of forming the second cavity structure (41) contains the pressure in the second cavity structure (14) being less than 10% or less than 1% of the ambient atmospheric pressure.

The method according to aspect 22, wherein the optical filter (39) is embodied monolithically with the substrate arrangement.

The method according to aspect 22, wherein the optical filter (39) is arranged at a third partial substrate arrangement ($S_3$) and this third partial substrate arrangement ($S_3$) is connected to the substrate arrangement.

The method according to aspect 17, including providing at least one electrical connector (51) for contacting the first circuit arrangement (11) and at least one electrical connector (52) for contacting the second circuit arrangement (12), wherein contact areas (53) of the electrical connectors (51, 52) are arranged at a portion of the substrate arrangement having the second circuit arrangement (12).

The method according to aspect 26, including forming at least one via (55) that extends through the substrate arrangement, said via connecting a contact area (53) of the at least one electrical connector (51) for contacting the first circuit arrangement (ii) to the first circuit arrangement (ii) in an electrically conductive manner, and filling this via (55) with an electrically and thermally conductive material.

The method according to aspect 27, further including forming a multiplicity of vias (55) that are arranged laterally around the cavity structure (14) and filled with electrically and thermally conductive material.

The method according to aspect 27, wherein the step of forming at least one via (55) contains arranging the at least one via (55) in relation to the cavity (14) in such a way that a distance ($D_1$) between the via (55) and the cavity structure (14) is less than a distance ($D_2$) between the via (55) and an outer side of the substrate arrangement.

A method including the following steps: providing a first wafer substrate (31) with a first side (30A) and an opposing second side (30B), wherein a heat distribution layer (33) is arranged on the first side (30A), structuring a heating element (35) on the heat distribution layer (33), etching a cavity (14) into the second side (30B) of the first wafer substrate (31) and arranging a heat reflection layer (43) at the base of the cavity (14), providing a second wafer substrate (44) with an integrated circuit (12), and bonding the first and the second wafer substrate (31, 44), wherein the cavity (14) forms a closed cavity that is arranged between the integrated circuit (12) and the heat distribution layer (33) and that has a pressure that is lower than the ambient atmospheric pressure.

Even though some aspects were described in conjunction with an apparatus, it is understood that these aspects also represent a description of the corresponding method, and so a block or a component of an apparatus should also be understood to be a corresponding method step or a feature of a method step. In an analogous fashion thereto, aspects that were described in conjunction with, or as, a method step also represent a description of a corresponding block or detail or feature of a corresponding apparatus. Some or all of the method steps can be carried out by a hardware device (or using a hardware device), such as e.g. a microprocessor, a programmable computer or an electronic circuit. In some exemplary embodiments, some or more of the most important method steps can be carried out by such a device.

Depending on certain requirements for implementation, exemplary embodiments of the invention can be implemented in hardware or in software or at least partly in hardware or at least partly in software. The implementation can be carried out using a digital storage medium, for example a floppy disk, a DVD, a Blu-ray disc, a CD, a ROM, a PROM, an EPROM, an EEPROM or a flash memory, a hard disk drive or any other magnetic or optical storage, on which electronically readable control signals are stored, said electronically readable control signals being able to interact or interacting with a programmable computer system in such a way that the respective method is carried out. Therefore, the digital storage medium may be computer-readable.

Thus, some exemplary embodiments according to the invention comprise a data medium which has electronically readable control signals that are able to interact with a programmable computer system in such a way that one of the methods described herein is carried out.

In general, exemplary embodiments of the present invention can be implemented as a computer program product with a program code, with the program code being effective to the effect of carrying out one of the methods when the computer program product is executed on a computer.

By way of example, the program code may also be stored on a machine-readable medium.

Other exemplary embodiments comprise the computer program for carrying out one of the methods described herein, wherein the computer program is stored on a machine-readable medium. Expressed differently, an exemplary embodiment of the method according to the invention is consequently a computer program which has a program code for carrying out one of the methods described herein when the computer program is executed on a computer.

Consequently, a further exemplary embodiment of the methods according to the invention is a data medium (or digital storage medium or computer-readable medium), on which the computer program for carrying out one of the methods described herein is recorded. The data medium or the digital storage medium or the computer-readable medium are typically physical and/or non-volatile.

Consequently, a further exemplary embodiment of the method according to the invention is a data stream or a sequence of signals which represents the computer program for carrying out one of the methods described herein. By way of example, the data stream or the sequence of signals can be configured to the effect of being transferred by way of a data communication link, for example by way of the Internet.

A further exemplary embodiment comprises a processing device, for example a computer or programmable logic component, which is configured or adapted to the effect of carrying out one of the methods described herein.

A further exemplary embodiment comprises a computer on which the computer program for carrying out one of the methods described herein is installed.

A further exemplary embodiment according to the invention comprises an apparatus or system that is configured to transfer a computer program for carrying out at least one of the methods described herein to a receiver. By way of example, transfer can be effectuated electronically or optically. By way of example, the receiver can be a computer, a mobile appliance, a storage appliance or a similar apparatus. By way of example, the apparatus or the system can comprise a fileserver for transferring the computer program to the receiver.

In some exemplary embodiments, a programmable logic component (for example a field-programmable gate array, an FPGA) can be used to carry out some or all functionalities of the methods described herein. In the case of some exemplary embodiments, a field-programmable gate array can interact with a microprocessor in order to carry out one of the methods described herein. In general, the methods are carried out on the part of any hardware apparatus in some exemplary embodiments. This may be universally employable hardware such as a computer processor (CPU) or hardware that is specific to the method, such as e.g. an ASIC.

The above-described exemplary embodiments only represent an illustration of the principles of the present invention. It is understood that modifications and variations of the arrangements and details described herein will be clear to other persons skilled in the art. Therefore, it is intended that the invention is only limited by the scope of protection of the following patent claims and not by the specific details that were presented on the basis of the description and the explanation of the exemplary embodiments herein.

What is claimed is:

1. An apparatus comprising:
    a substrate arrangement with a first circuit arrangement that heats up during operation and a second circuit arrangement that is integrated into a substrate material of the substrate arrangement; and
    a cavity structure that is arranged between the first and the second circuit arrangement, said cavity structure being formed in the substrate material and having a pressure that is lower than an ambient atmospheric pressure, wherein the apparatus has an optical filter that is embodied to filter electromagnetic radiation emitted by the first circuit arrangement, wherein the optical filter is arranged downstream of the first circuit arrangement in a principal emission direction of the electromagnetic radiation, and wherein a second cavity structure is formed between the first circuit arrangement and the optical filter, said second cavity structure having a lower pressure than the ambient atmospheric pressure.

2. The apparatus as claimed in claim 1, wherein the pressure in the cavity structure is less than 10% or less than 1% of the ambient atmosphere pressure.

3. The apparatus as claimed in claim 1, wherein:
    the cavity structure extends in a lateral direction between the first circuit arrangement and the second circuit arrangement; and at least the first circuit arrangement or the second circuit arrangement is arranged completely within a projection of the cavity structure perpendicular to this lateral direction of extent.

4. The apparatus as claimed in claim 1, wherein the substrate arrangement has two partial substrate arrangements that are stacked over one another, wherein a first partial substrate arrangement has the first circuit arrangement and a second partial substrate arrangement has the second circuit arrangement, and the cavity structure is formed as a sealed recess in at least one of the two partial substrate arrangements.

5. The apparatus as claimed in claim 1, wherein the apparatus has a heat distribution element that is coupled to the first circuit arrangement and embodied to distribute heat produced by the first circuit arrangement approximately uniformly over an entire surface of the heat distribution element.

6. The apparatus as claimed in claim 1, wherein the first circuit arrangement has an IR emitter.

7. The apparatus as claimed in claim 1, wherein the apparatus has a reflection arrangement for reflecting thermal radiation emitted by the first circuit arrangement, wherein the reflection arrangement is arranged within the cavity structure on a surface region of the cavity structure that faces the first circuit arrangement.

8. The apparatus as claimed in claim 1, wherein the pressure in the second cavity structure is less than 10% or less than 1% of the ambient atmospheric pressure.

9. The apparatus as claimed in claim 1, wherein the optical filter has a monolithic embodiment with the substrate arrangement.

10. The apparatus as claimed in claim 1, wherein the optical filter is arranged at a third partial substrate arrangement and this third partial substrate arrangement is connected to the substrate arrangement.

11. The apparatus as claimed in claim 1, wherein the substrate arrangement has at least one electrical connector for contacting the first circuit arrangement and at least one electrical connector for contacting the second circuit arrangement, wherein contact areas of the electrical connectors are arranged at a portion of the substrate arrangement having the second circuit arrangement.

12. The apparatus as claimed in claim 11, wherein a via is formed through the substrate arrangement, said via connecting a contact area of the at least one electrical connector for contacting the first circuit arrangement to the second circuit arrangement in an electrically conductive manner, wherein this via is filled with a thermally and electrically conductive material.

13. The apparatus as claimed in claim 12, wherein the apparatus has a multiplicity of vias that are arranged laterally around the cavity structure and filled with a thermally and electrically conductive material.

14. The apparatus as claimed in claim 11, wherein a distance between the via and the cavity structure is less than a distance between the via and an outer side of the substrate arrangement.

15. A wafer stack having a multiplicity of apparatuses as claimed in claim 1.

16. A method including the following steps:
providing a substrate arrangement with a first circuit arrangement that heats up during operation and a second circuit arrangement that is integrated into a substrate material of the substrate arrangement;
forming a cavity structure that is arranged between the first and the second circuit arrangement in the substrate material, wherein the cavity structure has a pressure that is lower than an ambient atmospheric pressure; and
providing an optical filter that is embodied to filter electromagnetic radiation emitted by the first circuit arrangement, wherein the optical filter is arranged downstream of the first circuit arrangement in a principal emission direction of the electromagnetic radiation, and forming a second cavity structure between the first circuit arrangement and the optical filter, wherein the second cavity structure has a lower pressure than the ambient atmospheric pressure.

17. The method as claimed in claim 16, wherein the step of forming the cavity structure comprises causing the pressure in the cavity structure to be less than 10% of the ambient atmospheric pressure.

18. The method as claimed in claim 16, wherein the step of providing the substrate arrangement comprises stacking two partial substrate arrangements over one another, wherein a first partial substrate arrangement has the first circuit arrangement and a second partial substrate arrangement has the second circuit arrangement, and wherein the step of forming the cavity structure comprises forming the cavity structure as a sealed recess in at least one of the two partial substrate arrangements.

19. The method as claimed in claim 18, wherein the first partial substrate arrangement and the second partial substrate arrangement are connected to one another using a vacuum bonding method.

20. The method as claimed in claim 16, further comprising providing a reflection arrangement for reflecting thermal radiation emitted by the first circuit arrangement, wherein the reflection arrangement is arranged within the cavity structure at a surface region of the cavity structure that faces the first circuit arrangement.

21. The method as claimed in claim 16, wherein the step of forming the second cavity structure comprises causing the pressure in the second cavity structure to be less than 10% of the ambient atmospheric pressure.

22. The method as claimed in claim 16, wherein the optical filter is embodied monolithically with the substrate arrangement.

23. The method as claimed in claim 16, wherein the optical filter is arranged at a third partial substrate arrangement, wherein the third partial substrate arrangement is connected to the substrate arrangement.

24. The method as claimed in claim 16, further comprising providing at least one electrical connector for contacting the first circuit arrangement and at least one electrical connector for contacting the second circuit arrangement, wherein contact areas of the electrical connectors are arranged at a portion of the substrate arrangement having the second circuit arrangement.

25. The method as claimed in claim 24, further comprising forming at least one via that extends through the substrate arrangement, said via connecting a contact area of the at least one electrical connector for contacting the first circuit arrangement to the first circuit arrangement in an electrically conductive manner, and filling the at least one via with an electrically and thermally conductive material.

26. The method as claimed in claim 25, further including forming a multiplicity of vias that are arranged laterally around the cavity structure and filling the multiplicity of vias with the electrically and thermally conductive material.

27. The method as claimed in claim 25, wherein the step of forming at least one via contains arranging the at least one via in relation to the cavity structure in such a way that a distance between the via and the cavity structure is less than a distance between the via and an outer side of the substrate arrangement.

28. An apparatus comprising:
- a substrate arrangement with a first circuit arrangement that heats up during operation and a second circuit arrangement that is integrated into a substrate material of the substrate arrangement; and
- a cavity structure that is arranged between the first and the second circuit arrangement, said cavity structure being formed in the substrate material and having a pressure that is lower than an ambient atmospheric pressure, wherein the apparatus has a reflection arrangement for reflecting thermal radiation emitted by the first circuit arrangement, wherein the reflection arrangement is arranged within the cavity structure on a surface region of the cavity structure that faces the first circuit arrangement.

29. A method including the following steps:
- providing a substrate arrangement with a first circuit arrangement that heats up during operation and a second circuit arrangement that is integrated into a substrate material of the substrate arrangement;
- forming a cavity structure that is arranged between the first and the second circuit arrangement in the substrate material, wherein the cavity structure has a pressure that is lower than an ambient atmospheric pressure; and
- providing a reflection arrangement for reflecting thermal radiation emitted by the first circuit arrangement, wherein the reflection arrangement is arranged within the cavity structure at a surface region of the cavity structure that faces the first circuit arrangement.

* * * * *